US00PP15794P2

(12) United States Plant Patent
Olesen et al.

(10) Patent No.: US PP15,794 P2
(45) Date of Patent: Jun. 14, 2005

(54) ROSE PLANT NAMED 'POULAC007'

(50) Latin Name: *Rosa hybrida*
Varietal Denomination: POULac007

(75) Inventors: L. Pernille Olesen, Fredensborg (DK); Mogens N. Olesen, Fredensborg (DK)

(73) Assignee: Poulsen Rosen A/S, Fredensborg (DK)

( * ) Notice: Subject to any disclaimer, the term of this patent is extended or adjusted under 35 U.S.C. 154(b) by 246 days.

(21) Appl. No.: 10/738,152

(22) Filed: Dec. 16, 2003

(51) Int. Cl.[7] ..... A01H 5/00
(52) U.S. Cl. ..... Plt./148
(58) Field of Search ..... Plt./148

*Primary Examiner*—Kent Bell
*Assistant Examiner*—S B. McCormick-Ewoldt

(57) ABSTRACT

A new garden rose plant of the compact floribunda class which has abundant, pink and apricot blend flowers and attractive foliage. This new and distinct variety has shown to be uniform and stable in the resulting generations from asexual propagation.

2 Drawing Sheets

Botanical classification: *Rosa hybrida.*
Variety demonination: 'POULac007'.

SUMMARY OF THE INVENTION

The present invention constitutes a new and distinct variety of garden rose plant which originated from a controlled crossing between the female parent plant, an unnamed seedling, and the male parent 'POULmax', described and illustrated in U.S. Plant patent application Ser. No. 10/192,746 dated Jul. 9, 2002. The two parents were crossed during the summer of 1993 and the resulting seeds were planted in a controlled environment in Fredensborg, Denmark. The new variety is named 'POULac007'.

The new variety may be distinguished from its seed parent, an unnamed variety by the following combination of characteristics:

1. The seed parent has a dark pink bud color as sepals unfold. 'POULac007' has a light pink bud color as sepals unfold.
2. While the seed parent has an average flower diameter of 60 mm. 'POULac007' has an average flower diameter of 70 mm to 75 mm.

The new variety may be distinguished from its pollen parent, 'POULmax' by the following combination of characteristics:

1. The pollen parent has Red Group 46C to 47D flower bud color, as sepals divide to ¼ open. 'POULac007' has Red Group 55D flower bud color, as sepals divide to ¼ open.
2. The pollen parent has a petalage count of 18 to 22 petals. 'POULac007' has a petalage count of 66 petals.

The objective of the hybridization of this rose variety was to create a new and distinct variety for garden use with unique qualities, such as:

1. Uniform and abundant light pink flowers;
2. Vigorous, but compact growth when propagated both as a budded rose and on its own roots;
3. Disease resistance.

This combination of qualities is not present in previously available commercial cultivars of this type, known to the inventors, and distinguish 'POULac007' from all other varieties of which we are aware.

As part of their rose development program, L. Pernille Olesen and Mogens N. Olesen germinated the seeds from the aforementioned hybridization during winter 1993 and conducted evaluations on the resulting seedlings in a controlled environment in Fredensborg, Denmark.

'POULac007' was selected in the spring 1994 by the inventors as a single plant from the progeny of the aforementioned hybridization.

Asexual reproduction of 'POULac007' by traditional budding and rooted cuttings was first done by L. Pernille and Mogens N. Olesen in their nursery in Fredensborg, Denmark in July, 1994. This initial and other subsequent asexual propagations conducted in controlled environments have demonstrated that the characteristics of 'POULac007' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULac007'. Specifically illustrated in SHEET 1:

FIG. 1.2; Flower bud closed and flower bud partially open;

FIG. 1.3; Flower petals, detached;

Specifically illustrated in SHEET 2:

FIG. 2.1; Sepals, receptacle, and peduncle;

FIG. 2.2; Bare stems exhibiting thorns;

FIG. 2.3; Mature Leaves.

DETAILED DESCRIPTION OF THE VARIETY

Figures 1A, 1B, 1C:
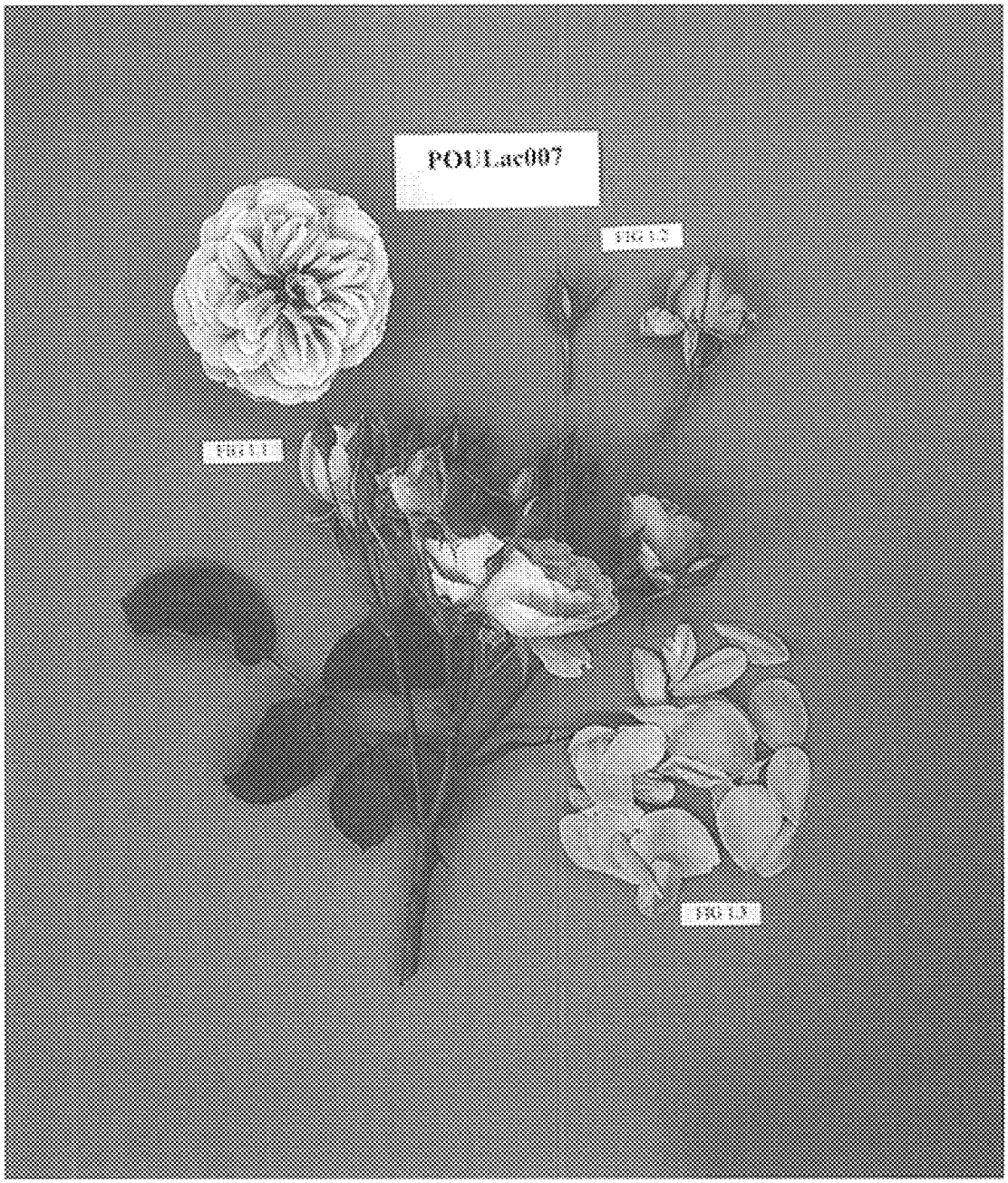
FIG. 1.1; Open flower, stem showing open flower, branching, and the attachment of leaves, buds, and peduncles.

The following is a description of 'POULac007', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULelap', a rose variety from the same inventors described and illustrated in U.S. Plant Pat. No. 10,821 and issued on Mar. 9, 1999, are compared to 'POULac007' in Chart 1.

CHART 1

| | 'POULac007' | 'POULelap' |
|---|---|---|
| Upon opening, the inner side of the outermost petals | Red Group 49C | Orange Group 27D. |
| Receptacle Color. | Yellow-Green Group 144B. | Green Group 143C. |
| Average flower diameter. | 70 mm to 75 mm when open. | 60 to 70 mm when open. |

Parents:
*Seed parent.*—Unnamed seedling.
*Pollen parent.*—'POULmax'.

FLOWER AND FLOWER BUD

Blooming habit:Continuous.
Flower bud:
*Size.*—Upon opening, 33 mm in length from base of receptacle to end of bud.
*Bud form.*—Point ovoid.
*Bud color.*—As sepals unfold, petals are Red Group 55D. At ¼ opening petals are Red Group 55D.
*Sepals.*—Upper Surface: Color: Green Group 139C. Lower Surface: Color: Yellow-Green Group 144A to 144B. Shape: Sepal apex is cirrhose. Base is flat at union with receptacle. Margins: Entire. Very weak or absent foliaceous appendages on three of the five sepals. Size: 30 mm (l) by 6 mm (w).
*Receptacle.*—Surface: Smooth. Shape: Urn-shaped. Size: 8 mm (h)×8 mm (w). Color: Yellow-Green Group 148B. Anthocyanin: None observed.
*Peduncle.*—Surface: Smooth. Moderate occurrence of stipitate glands observed. Length: 35 mm to 42 mm. Color: Yellow Group 144C. Anthocyanic pigments the color of Greyed-Purple Group 184C observed. Strength: Somewhat strong.
*Borne.*—Varying from 4 to 12 flower buds per stem.
Flower bloom:
*Fragrance.*—Very light rose scent.
*Duration.*—The blooms have a duration on the plant of approximately 10 days. Afterwards, petals fall cleanly away from plant.
*Size.*—Flower diameter is 70 to 75 mm when open.
*Form.*—General Shape: Rosette. Shape of flower when viewed from the side: Upon opening, upper part:Flat. Upon opening, lower part:Flat to slightly concave. Open flower, upper part: Flattened convex. Open flower, lower part: Concave.
Petalage: On average range: 66 petals under normal conditions with 10 to 15 petaloids.
Color: Upon opening, petals:
*Outermost petals.*—Outer side: Red Group 55D. Inner Side: Red Group 49C.
*Innermost petals.*—Outer side: Red Group 49D. Inner Side: Red Group 49D.
Upon opening, basal petal spots:
*Outermost petals.*—Outer side: Yellow Group 11D. Inner Side: Yellow Group 11B.
*Innermost petals.*—Outer side: Yellow Group 11D. Inner Side: Yellow Group 11B.
After opening, petals:
*Outermost petals.*—Outer side: Red Group 56C. Inner Side: Red Group 36C.
*Innermost petals.*—Outer side: Red Group 56A. Inner Side: Red Group 56C.
After opening, basal petal spots:
*Outermost petals.*—Outer Side: Yellow Group 9C. Inner Side: Yellow Group 7D.
*Innermost petals.*—Outer Side: Yellow Group 9D. Inner Side: Yellow Group 7D.
General tonality: On open flower Red Group 50D. No change in the general tonality at the end of the $7^{th}$ day.
Petals:
*Petal reflex.*—Absent.
*Margin.*—Entire with very weak undulations.
*Size.*—36 to 40 mm in length by 31 to 39 mm wide.
*Shape.*—Deltoid. Apex: Round. Base: Acute.
*Texture.*—Smooth.
*Thickness.*—Thin.
*Arrangement.*—Not Formal.
Petaloids:
*Quantity.*—10 to 15.
*Color.*—Red Group 36D on upper and lower surfaces.
*Size.*—29 to 32 mm in length by 10 to 17 mm wide.
Reproductive organs:
*Pistils.*—Length: 8 long. Quantity: 35 (actual count).
*Pollen.*—Color: Greyed-Orange Group 163B. Quantity: Average.
*Anthers.*—Size: 2 mm long. Color: Greyed-Yellow Group 162A at margins with mid section Red Group 37A. Quantity: 52 (actual count).
*Filaments.*—Color: Yellow Group 12A. Length: 6 mm.
*Stigmas.*—Equal in height relative to the anthers. Color: Greyed-Yellow Group 161D. Size: 2 mm.
*Styles.*—Color: Greyed-Yellow Group 161D. Other Intonations: None.
*Hips.*—None Observed in the field nursery in Jackson County Oreg.

PLANT

Plant growth: Moderate, upright to bushy. When grown as a budded field grown plant on *Rosa multiflora* understock, the average height of the plant is 40 cm to 60 cm.
Stems:
*Color.*—Young wood: Yellow-Green Group 144B. Older wood: Yellow-Green Group 144B.
*Surface texture.*—Young wood: Smooth. Older wood: Smooth.
*Thorns.*—Incidence: 14 thorns per 10 cm of stem. Size: Average length: 8 mm. Color: Greyed-Purple Group 184A with intonations of Yellow-Green Group 144B. Shape: Deeply concave.
Plant foliage: Normal number of leaflets on normal leaves in middle of the stem: 7 leaflets.
*Compound leaf size.*—165 mm (l)×120 mm (w).
*Quantity.*—Six leaves per 10 cm of stem on average.
*Color.*—Mature Foliage: Upper Leaf Surface: Yellow-Green Group 144A to Yellow-Green Group 146A. Lower Leaf Surface: Yellow-Green Group 146B to Yellow-Green Group 146C. Juvenile foliage: Upper Leaf Surface: Yellow-Green Group 144A to Yellow- Green Group 146A. Lower Leaf Surface: Yellow-Green Group 146B to Yellow-Green Group 146C. Anthocyanin: None.

Plant leaves and leaflets:

*Stipules.*—Size: 16 mm in length. Color: Yellow-Green Group 144A. Margins: Finely serrated with moderate to heavy stipitate glands. Anthocyanin: Color: Greyed-Purple Group 183C.

*Petiole.*—Length: 30 mm to 35 mm. Color: Yellow-Green Group 144A. Underneath: Small prickles observed. Margins: Stipitate glands present. Anthocyanin: None observed.

*Rachis.*—Color: Yellow-Green Group 144A. Underneath: Prickles, 2 mm in length observed. Margins: Stipitate glands observed.

*Leaflet.*—Size: 35 to 50 mm (l)×25 to 30 mm (w). Edge: Serrated. Shape: Ovate. Texture: Smooth. Arrangement: Odd pinnate. Venation: Reticulate. Glossiness: Moderately glossy to matte finish.

Disease resistance: Above average resistance to mildew, rust, black spot, and Botrytis under normal growing conditions in Jackson County, Oreg.

Cold hardiness: The variety 'POULac007' has been found to be cold tolerant to USDA Cold Hardiness Zone 6.

We claim:

1. A new and distinct variety of rose plant of the compact floribunda rose class, substantially as herein illustrated and described as a distinct and novel rose variety due to its abundant pink and apricot blend flowers, disease resistance, and extended period of bloom.

* * * * *

POULac007

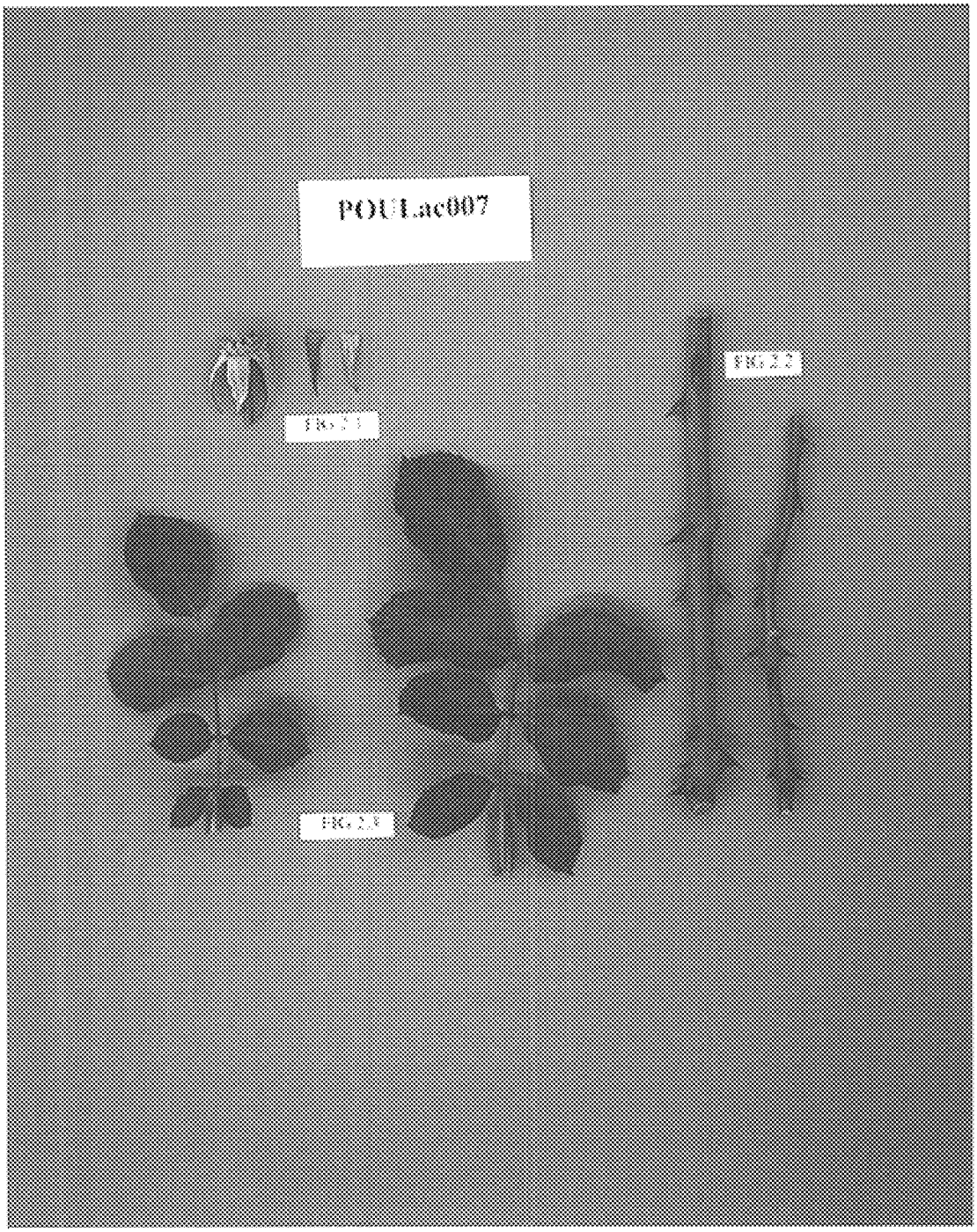
POULac007
FIG. 2.1
FIG. 2.2
FIG. 2.3